(12) United States Patent
Tandon et al.

(10) Patent No.: US 12,121,197 B2
(45) Date of Patent: Oct. 22, 2024

(54) ENTRYWAY MAT FOR DISINFECTING THE SOLES OF SHOES

(71) Applicants: Abhishek Tandon, Dallas, TX (US); Kanak Subramanian, Dallas, TX (US)

(72) Inventors: Abhishek Tandon, Dallas, TX (US); Kanak Subramanian, Dallas, TX (US)

( * ) Notice: Subject to any disclaimer, the term of this patent is extended or adjusted under 35 U.S.C. 154(b) by 351 days.

(21) Appl. No.: 17/491,921

(22) Filed: Oct. 1, 2021

(65) Prior Publication Data

US 2022/0104686 A1 Apr. 7, 2022

Related U.S. Application Data

(60) Provisional application No. 63/086,635, filed on Oct. 2, 2020.

(51) Int. Cl.
*A47L 23/26* (2006.01)
*A47L 23/02* (2006.01)
*A47L 23/20* (2006.01)
*A61L 2/22* (2006.01)

(52) U.S. Cl.
CPC ............ *A47L 23/266* (2013.01); *A47L 23/02* (2013.01); *A47L 23/20* (2013.01); *A61L 2/22* (2013.01); *A61L 2202/14* (2013.01); *A61L 2202/15* (2013.01)

(58) Field of Classification Search
CPC ........ A47L 23/02; A47L 23/26; A47L 23/266; A47L 23/263; A47L 23/20; A47L 23/22; A47L 23/205; A47L 23/24; A47L 23/00; A47L 23/18
USPC ........... 134/57 R; 15/36, 112, 161, 215, 238, 15/237, 30
See application file for complete search history.

(56) References Cited

U.S. PATENT DOCUMENTS

| | | | |
|---|---|---|---|
| 6,668,842 B1 * | 12/2003 | Wilke ............... | A47L 23/02 134/119 |
| 9,402,529 B1 | 8/2016 | Daniel | |
| 2010/0243087 A1 * | 9/2010 | Morrissey ........ | F04B 43/082 137/565.17 |
| 2012/0167325 A1 | 7/2012 | Omidi | |
| 2014/0116468 A1 * | 5/2014 | Craven ............. | A47L 23/02 134/34 |
| 2015/0096597 A1 * | 4/2015 | Patel ................ | A47L 23/266 134/18 |
| 2017/0035267 A1 * | 2/2017 | Bassiri ............. | A61L 2/18 |
| 2017/0095127 A1 * | 4/2017 | Castillo Sancho ........ | B05B 11/1052 |
| 2017/0128606 A1 | 5/2017 | Jackson | |
| 2018/0042449 A1 * | 2/2018 | Ori .................. | A47L 23/26 |
| 2020/0163532 A1 * | 5/2020 | George ............ | A47L 23/22 |

(Continued)

FOREIGN PATENT DOCUMENTS

WO WO 2016/0147087 A1 9/2016
WO WO-2019209917 A1 * 10/2019 ............ A47L 23/02

OTHER PUBLICATIONS

PCT International Search Report and Written Opinion, PCT/US2021/053126, Feb. 18, 2022.

*Primary Examiner* — David G Cormier
*Assistant Examiner* — Thomas Bucci
(74) *Attorney, Agent, or Firm* — Joseph T. Leone; DeWitt LLP

(57) ABSTRACT

An entryway mat with a misting area and a drying area. When a user steps on the misting area, a disinfecting solution is dispensed onto the bottoms of the user's feet. The user then steps onto the drying area to wipe away the disinfecting solution.

13 Claims, 13 Drawing Sheets

(56) References Cited

U.S. PATENT DOCUMENTS

2020/0275821 A1\* 9/2020 Busken-Jovanovich ............... B08B 3/02
2021/0316024 A1\* 10/2021 Green ................. A61L 2/24

\* cited by examiner

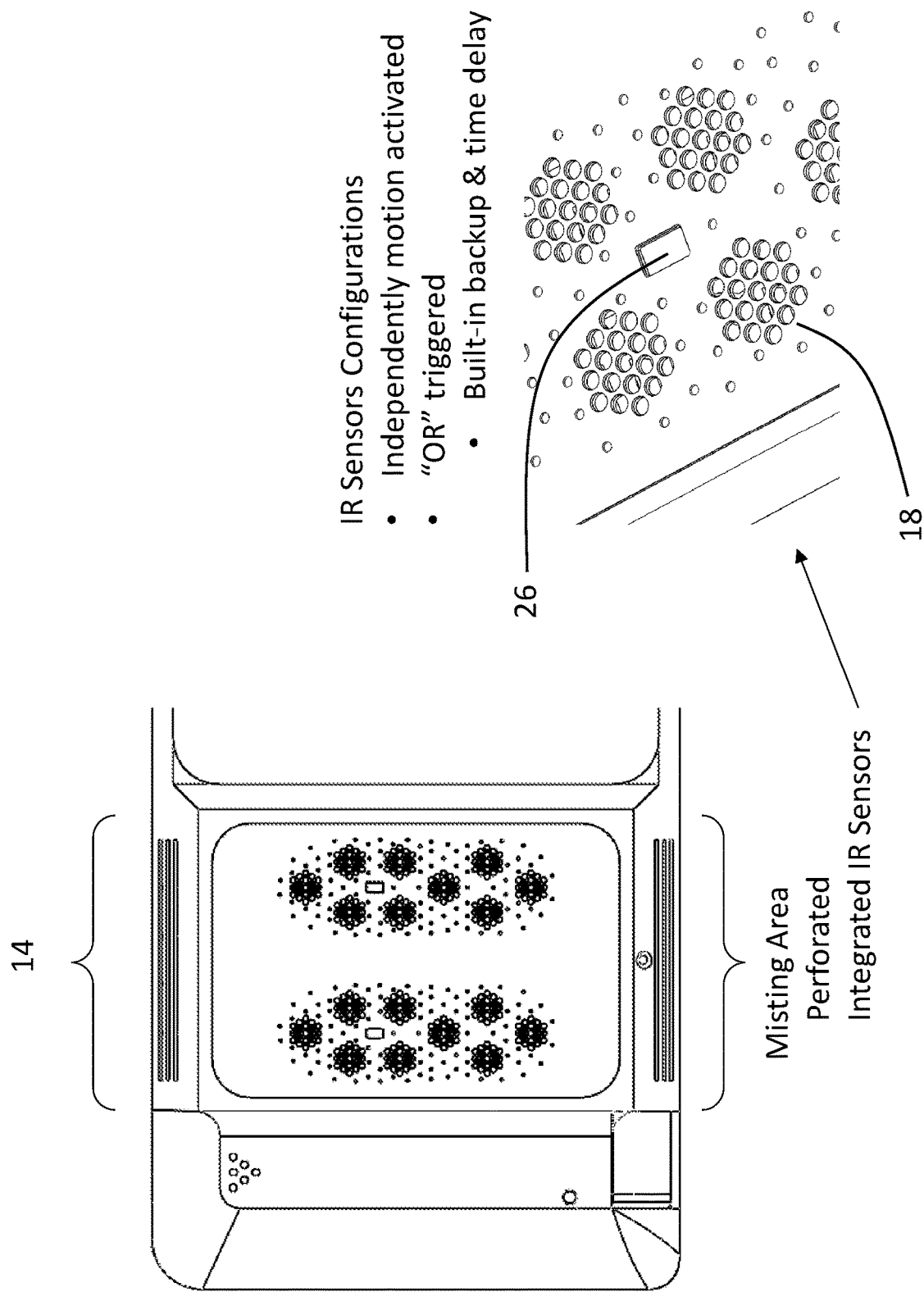

Alternative Misting System Configurations

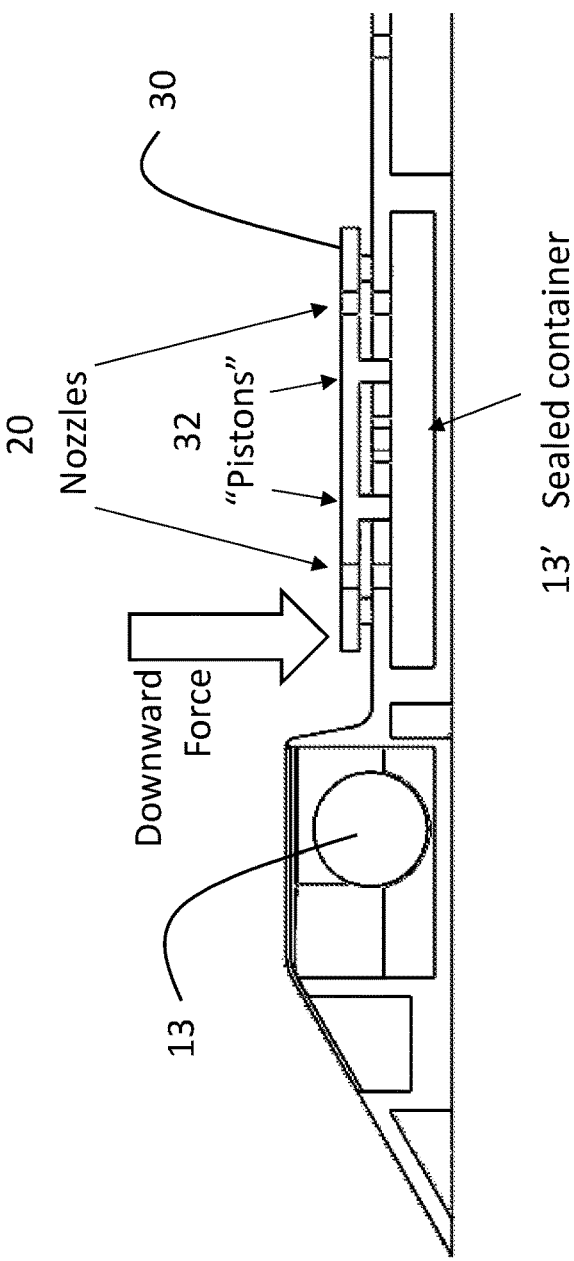

A downward force (user's weight) will cause the upper plate to move down decreasing the volume of the sealed container and increasing the pressure, which will cause the misting nozzles to mist. Once the weight is removed, springs will push the upper plate back up increasing the volume and decreasing the pressure creating a vacuum to pull more liquid into the container from the cylinder.

FIG. 9B

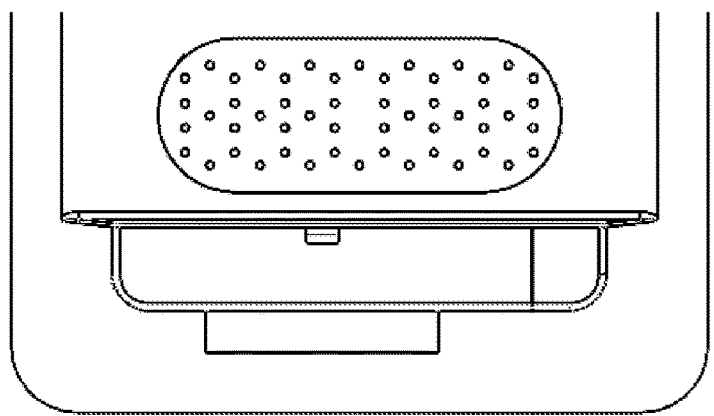

FIG. 9A

Regional Misting Configuration

Hyper-Regional Misting Configuration

Localized Misting Configuration

ENTRYWAY MAT FOR DISINFECTING THE SOLES OF SHOES

CROSS-REFERENCE TO RELATED APPLICATIONS

Priority is hereby claimed to provisional application Ser. No. 63/086,635, filed Oct. 2, 2020, which is incorporated herein by reference.

BACKGROUND

Various kinds of door mats and entryway mats have been used over the years to reduce or eliminate dirt, debris, and contaminants from entering an inside location, be it a home, a laboratory, or a cleanroom. For example, disposable entryway mats for clean rooms are a staple commodity. These are disposable items akin to a large tablet of paper. However, each sheet is made from a sticky/tacky material. The mats are used in the conventional fashion: They are placed on the floor in front of the door to a laboratory or clean room in such a fashion that people entering (or leaving) the space must place both feet onto the mat. The sticky coating used actively traps dirt and debris from the bottom of the shoes of those people passing over the mat. When the sheet starts to lose its stickiness (due to adhered debris) it is simply discarded and a new one installed in its place. Such mats are made by many suppliers, such as CleanPro Cleanroom Products (a division of Production Automation Corporation, Minnetonka, Minnesota).

Entryway mats that dispense a liquid cleaning/disinfecting solution onto the soles of shoes stepping onto the mat are known. See U.S. Pat. No. 9,402,529, issued Aug. 2, 2016, to Daniel. This device, however, is entirely gravity operated, and thus responds differently when people of differing weight tread upon it. That is, the amount of disinfecting liquid dispensed by the mat is directly proportional to the weight of the person stepping onto the mat. Also, because the mat does not include a separate space to dry the user's shoes, it does not accomplish its intended purpose. Once a user steps off the mat shown in Daniel, the user will track wet footprints throughout the area that is supposed to be kept clean.

SUMMARY

Disclosed is a smart and redesigned entryway mat. The mat comprises a housing defining a misting area (14) and a drying area (16), wherein the misting and drying areas are dimensioned and configured to support a human user standing on either area. The misting area includes a plurality of perforations passing through it. A misting cylinder (13) or misting bladder (13') containing a disinfecting solution at a pressure higher than atmospheric pressure and in fluid connection to one or more spray nozzles (20) is positioned in the housing. The spray nozzles (20) are dimensioned and configured to dispense the disinfecting solution through the perforations (18) in the misting area (14) and to contact the feet or the soles of the shoes of users standing on the misting area (14). The mat also comprises at least one sensor (26) operationally connected to at least one sensor-controlled valve (28), wherein the sensor-controlled valve (28) is operationally positioned between the misting cylinder (13) or misting bladder (13') and the one or more spray nozzles (20). The sensor is configured to open the sensor-controlled valve (28) when a user steps onto the misting area (14) and to close the sensor-controlled valve when the user steps off the misting area (14).

In certain versions of the entryway mat, the misting cylinder (13) or misting bladder (13') are refillable or replaceable.

In another version, the entryway mat further comprising a microcontroller (22) operationally connected to the sensor (26) and the sensor-controlled valve (28). The microcontroller (22) is pre-programmed to open the one sensor-controlled valve (28) for a pre-determined amount of time in response to a user stepping onto the misting area (14).

In yet another version of the entryway mat, the misting area (14) comprises a movable upper plate (30) and at least one piston (32) operationally connected to the movable upper plate (30) and the misting bladder (13'). The plate, piston, and bladder are arranged so that a user stepping onto the movable upper place (30) applies pressure to the misting bladder (13') via action of the piston (32).

In another version, the mat comprises a number of cones (34) corresponding to the number of spray nozzles (20), each cone having a narrow end attached to its corresponding nozzle and a wide end positioned in proximity to the perforations in the misting area. The cones function to direct the disinfecting solution onto the bottoms of the user's feet.

In yet another version, the entryway mat further comprising a microcontroller (22) operationally connected to the sensor (26) and the sensor-controlled valve (28) is also operationally connected to a motion sensor (35). The microcontroller (22) is pre-programmed to provide power to the sensor (26) and the sensor-controlled valve (28) for a predefined period of time when the motion sensor (35) detects motion and to not provide power to the sensor (26) and the sensor-controlled valve (28) when the motion sensor (35) does not detect motion after that predefined period of time has elapsed. The microcontroller (22) will also enter into a power-saving "sleep" mode after that predefined period of time has elapsed.

In another version, the mat comprising a microcontroller (22) operationally connected to a switch (36). The microcontroller (22) is pre-programmed to turn the system on or off when the switch (36) is pressed, opposite the current state. The microcontroller (22) operationally connected to the sensor-controlled valve (28) is able to be pre-programmed such when the switch (36) is pressed for a predefined period of time, the sensor-controlled valve (28) will open for as long as the switch (36) continues to remain pressed.

BRIEF DESCRIPTION OF THE DRAWINGS

FIG. 3A is a partial top plan, cutaway view of the mat showing the misting area 14.

FIG. 3B is a magnified view of FIG. 3A showing the perforations 18.

FIG. 9A is a top plan view of the piston-actuated misting sub-assembly. FIG. 9B is a front elevation cross-section view of the top plan view shown in FIG. 9A.

DETAILED DESCRIPTION

Figure 1:
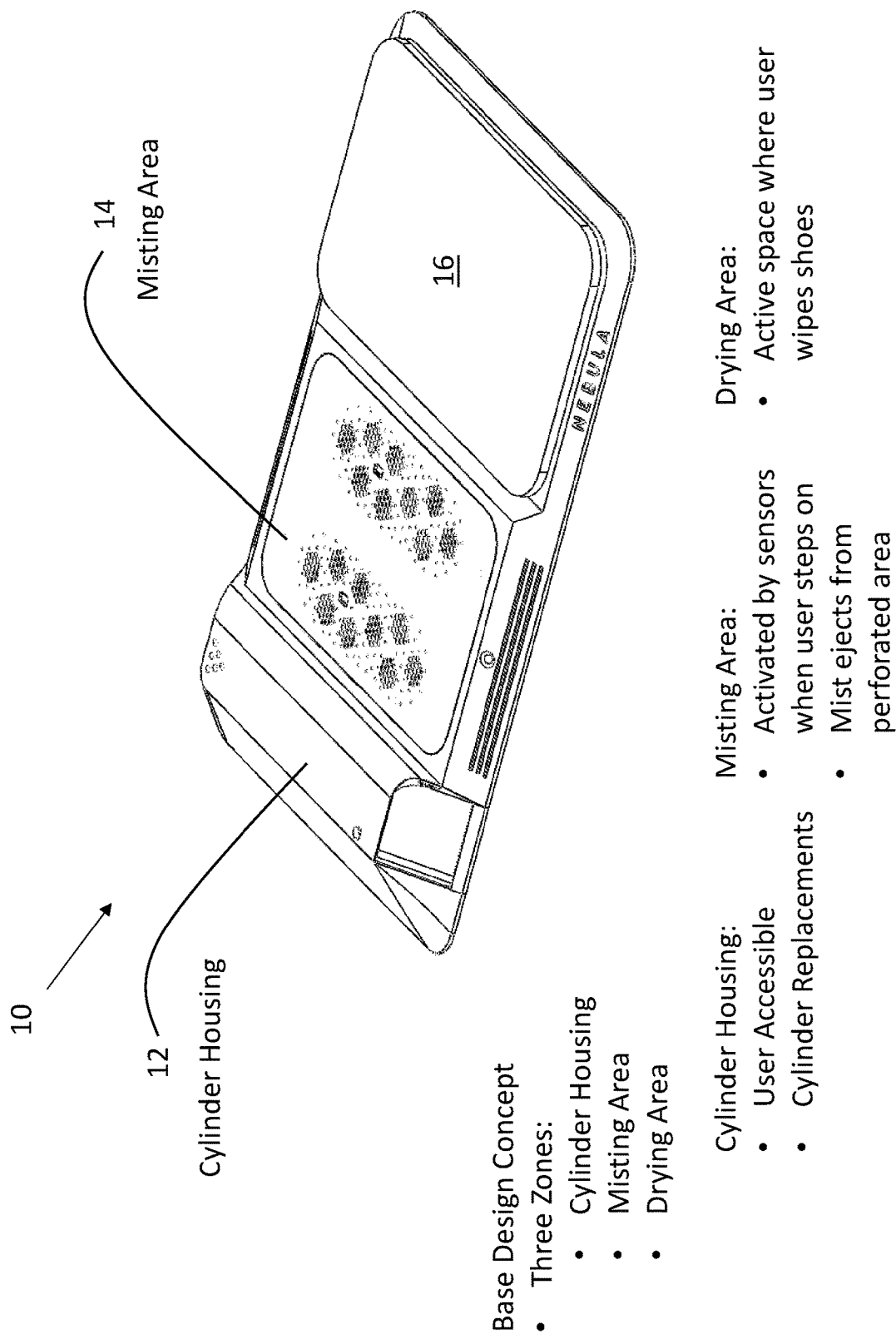
FIG. 1 is a top perspective view of an entryway mat as disclosed and claimed herein.

Referring now to the drawings, the same reference numerals are used throughout the drawings to identify the same or corresponding elements of the disclosed entryway mat. FIG. 1 depicts a top perspective view of a first version of the entryway mat 10 as disclosed and claimed herein. The mat comprising a housing (unnumbered) fabricated from any suitable material (e.g. metal, composite, wood, etc.), but preferably a conventional thermosetting or thermoplastic resin formulation. A host of such materials are well known in the art, and include, but are not limited to polyethylene terephthalate (PET), polyethylene (PE), polyvinyl chloride (PVC), polypropylene (PP), polystyrene (PS), polylactic acid (PLA), polycarbonate (PC), acrylic resins such as poly(methylmethacrylate) (PMMA), acetal resins such as polyoxymethylene (POM), polyamides such as Nylon-brand resins, and copolymers of the foregoing, for example acrylonitrile-butadiene-styrene (ABS). The overall entryway mat comprises three regions: (1) A cylinder housing 12. The cylinder housing contains a refillable or replaceable reservoir containing a cleaning/disinfecting solution to be sprayed onto the soles of the shoes of users of the mat. (The cleaning solution itself is conventional and will not be described herein.) (2) A misting area 14 defining a plurality of perforations 18 (see FIG. 3B). A user places both feet upon the misting area 14 to have the soles of his shoes cleaned and disinfected. As described herein, the cleaning solution is contained in a misting cylinder 13 (shown in FIG. 2 and positioned in the cylinder housing 12). Alternatively, the cleaning solution can be contained in an external attachment/casing to expand the capacity. The cleaning solution is dispensed under pressure from the misting cylinder 13, passes through the perforations in the misting area, and comes into contact with the soles of a user's shoes. The user then moves his feet from the misting area 14 to the drying area 16 to wipe the now-dirty cleaning solution from the soles of his shoes. In this fashion, the user then steps away from the entryway mat 10 and into the protected area with little to no dirt/debris/contaminant/germs left on the sole of the shoes. This effectively diminishes or eliminates the spread of the germs by shoe to floor contact.

The drying area 16 may comprise a tablet of multiple sheets of conventional, disposable drying media (for example, paper or cloth sheets). The drying media may be made sticky or tacky with a coating as is known in the art. Or the drying area may comprise a reusable fibrous or cloth material, such as a no-lint fabric that can be removed, washed, and replaced periodically. Similarly, the drying area may also comprise a biodegradable, renewable drying material, such as a jute or bamboo pad.

Figure 2B:
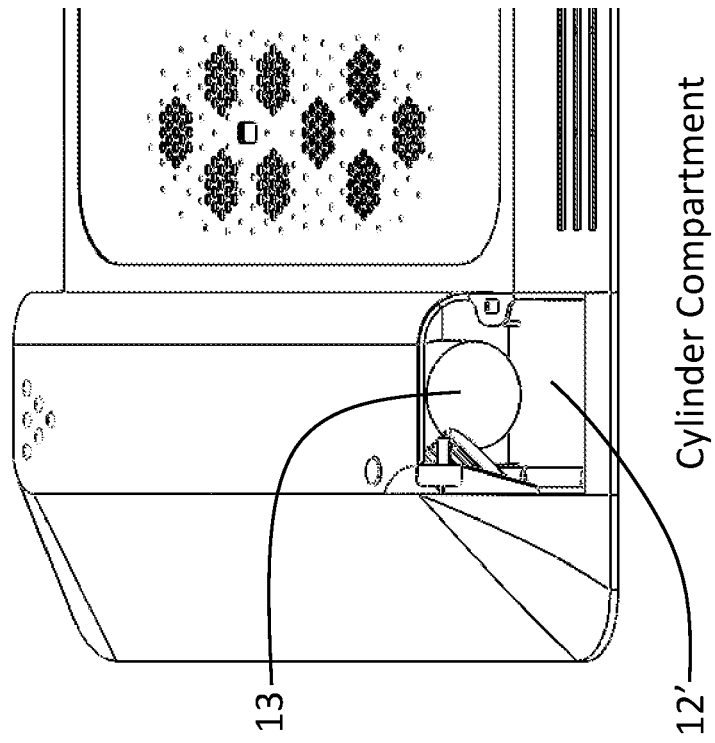
FIG. 2B is FIG. 2A with the cylinder housing compartment lid opened.
Figure 2A:
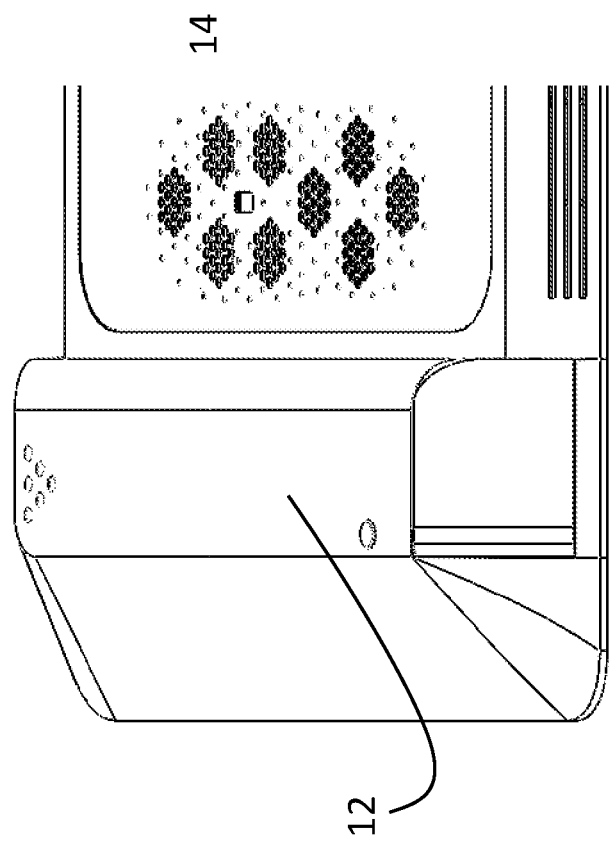
FIG. 2A is a partial angled top view of the mat showing the cylinder housing 12.

FIG. 2A is a partial angled top view of the mat showing the cylinder housing 12, while FIG. 2B is FIG. 2A with the cylinder housing lid opened. FIG. 2A depicts a magnified view of the cylinder housing 12. As shown in FIG. 2B, the cylinder housing 12 defines an interior compartment 12' which holds the misting cylinder 13. Alternatively, the cleaning solution can be contained in an external attachment/casing to expand the capacity.

The misting cylinder 13 is an aerosol-type pressure container of conventional design. The misting cylinder comprises a can or bottle or other pressure vessel that contains the cleaning solution as the "payload" and a propellant under pressure. When the container's valve is opened, the payload is forced out of a series of spray nozzles 20 (see FIG. 6) and emerges as an aerosol or mist. As propellant expands within the misting cylinder to drive out the payload, a portion of the propellant remaining inside the misting cylinder 13 evaporates, thereby maintaining a pressure higher than atmospheric pressure inside the misting cylinder 13. Once the propellant and its entrained payload exit the nozzles 20, the droplets of propellant evaporate rapidly, leaving the payload (the cleaning solution) suspended as very fine particles or droplets. Alternatively, in the case that the propellant remains a gas under pressure in the misting cylinder 13, the propellant pushes the payload through the nozzles 20 as very fine particles or droplets. These droplets of cleaning solution are then directed through the perforations 18 in the misting area 14 to contact the soles of user's shoes.

FIG. 3A is a partial top plan view of the mat showing the misting area 14. FIG. 3B is a magnified view of FIG. 3A. FIG. 3B show the perforations 18 that are defining characteristic of the misting area 14. The perforations are simple apertures. They are shown as being circular, but they may be of any suitable shape—ovals, triangles, squares, etc. The area of each perforation 18 is large enough to permit easy passage of the cleaning solution through each perforation, and small enough to maintain the structural rigidity of the misting area 14. The misting area is dimensioned and configured to function with the full-range of sizes of human users—from the small children to very large men. So the misting area 14 must be sufficiently rigid to support a weight of roughly 200 kg or more, distributed over the surface area defined by the bottom of two human feet. The perforations 18 are also depicted as being uniform in size and shape. This is simply a design choice. The multitude of perforations may be of different shapes and cross-sectional area. Visible through one of the perforations in FIG. 3B is a sensor 26. The sensor 26 may, for example be an optical sensor, such as an IR detector or other light beam detector, or a pressure sensor that detects the weight of a user who steps on the misting area.

Figure 4:
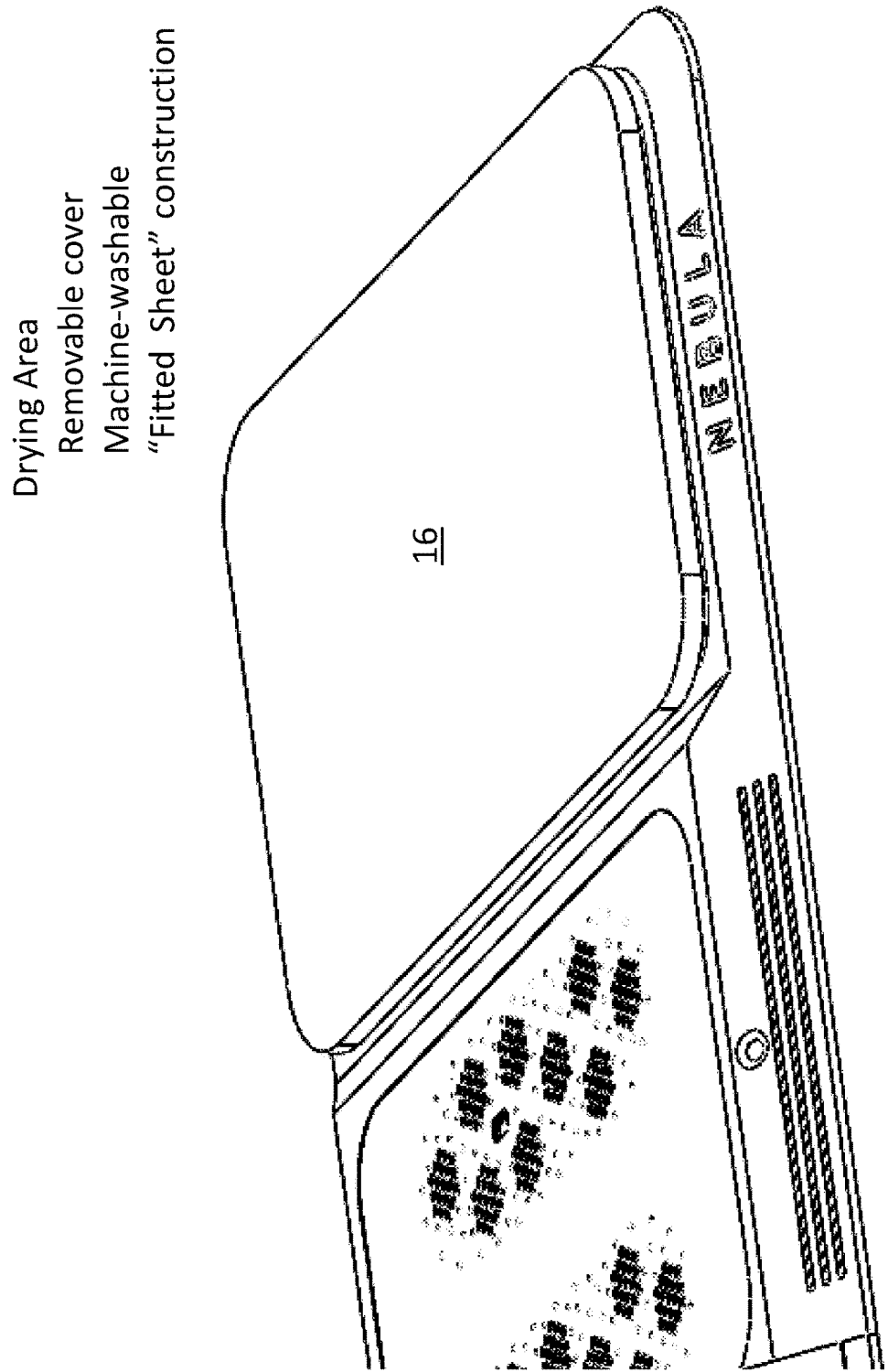
FIG. 4 is a top perspective view focusing on the drying area 16.

FIG. 4 is a top perspective view focusing on the drying area 16. As noted in the figure, one version of the drying area may be in the form of a "fitted sheet." That is, a cloth material, perhaps elasticized or having an elastic perimeter, that is stretched over the housing. This version of the drying area 16 is attractive because the area 16 will remain flat and "neat." Users are likely to rub their feet vigorously on drying area 16 to dry the soles of their shoes. A fitted sheet-like construction holds the material of the drying area 16 flat to the housing of the device. In addition, the material for the drying area 16 may be chosen to increase friction between the housing (unnumbered) and the cloth material to prevent shifting in the central area. As noted above, the actual material used in the drying mat may be any conventional material suitable for the intended purpose.

Figure 5:
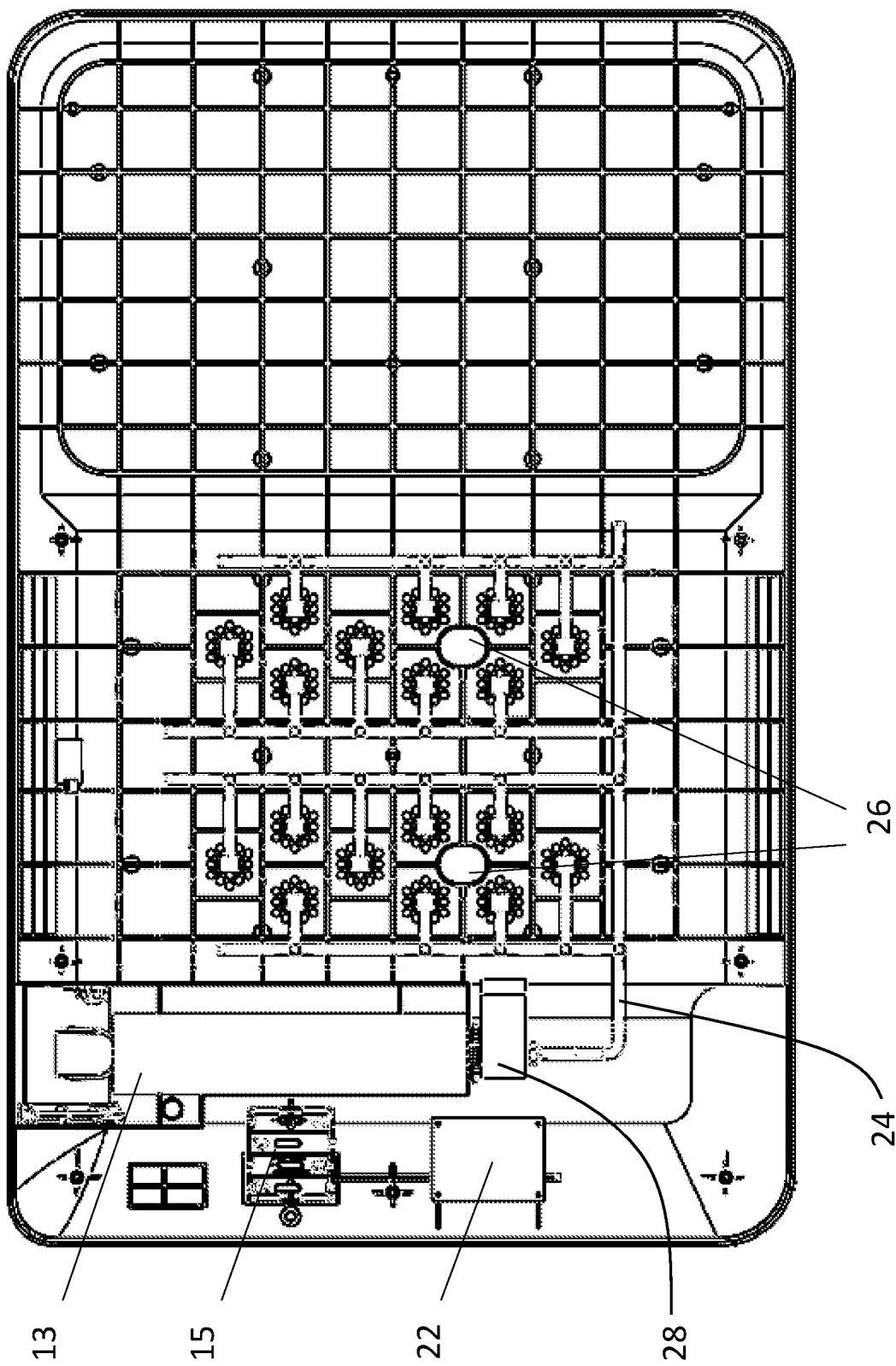
FIG. 5 is a cut-away bottom plan view of one version of the mat.

FIG. 5 is a cut-away bottom plan view of one version of the mat. The misting cylinder 13 can be seen as well as a battery compartment 15. In the bottom-left corner of the figure can be seen a valve 28, preferably a solenoid-activated valve, that is operationally linked to both the battery 15 and the misting cylinder 13. The valve 28 is dimensioned and configured to open and close the misting cylinder when a user steps on the misting area 14. This is done via one or more sensors 26 and a microcontroller 22, both of which are also operationally linked to the battery. The battery used may be of any conventional design and is dimensioned and configured to power the sensors 26 and 35 and open and close a valve to dispense cleaning fluid contained under pressure in the misting cylinder 13.

The sensor 26 and microcontroller 22 are of conventional design. The sensor 26 may, for example be an optical sensor, such as an IR detector or other light beam detector, or a pressure sensor that detects the weight of a user who steps on the misting area. The microcontroller 22 may be in the form of a printed circuit board (PCB). Such microcontrollers are conventional and well known in the art. The sensor 26 and microcontroller 22 are operationally linked to the valve 28 so that when a user steps on the misting area, the valve 28 is opened for a pre-determined amount of time and then closed. The length of time the valve 28 is open determines the amount of cleaning solution that is dispensed from the misting cylinder 13.

Figure 6:
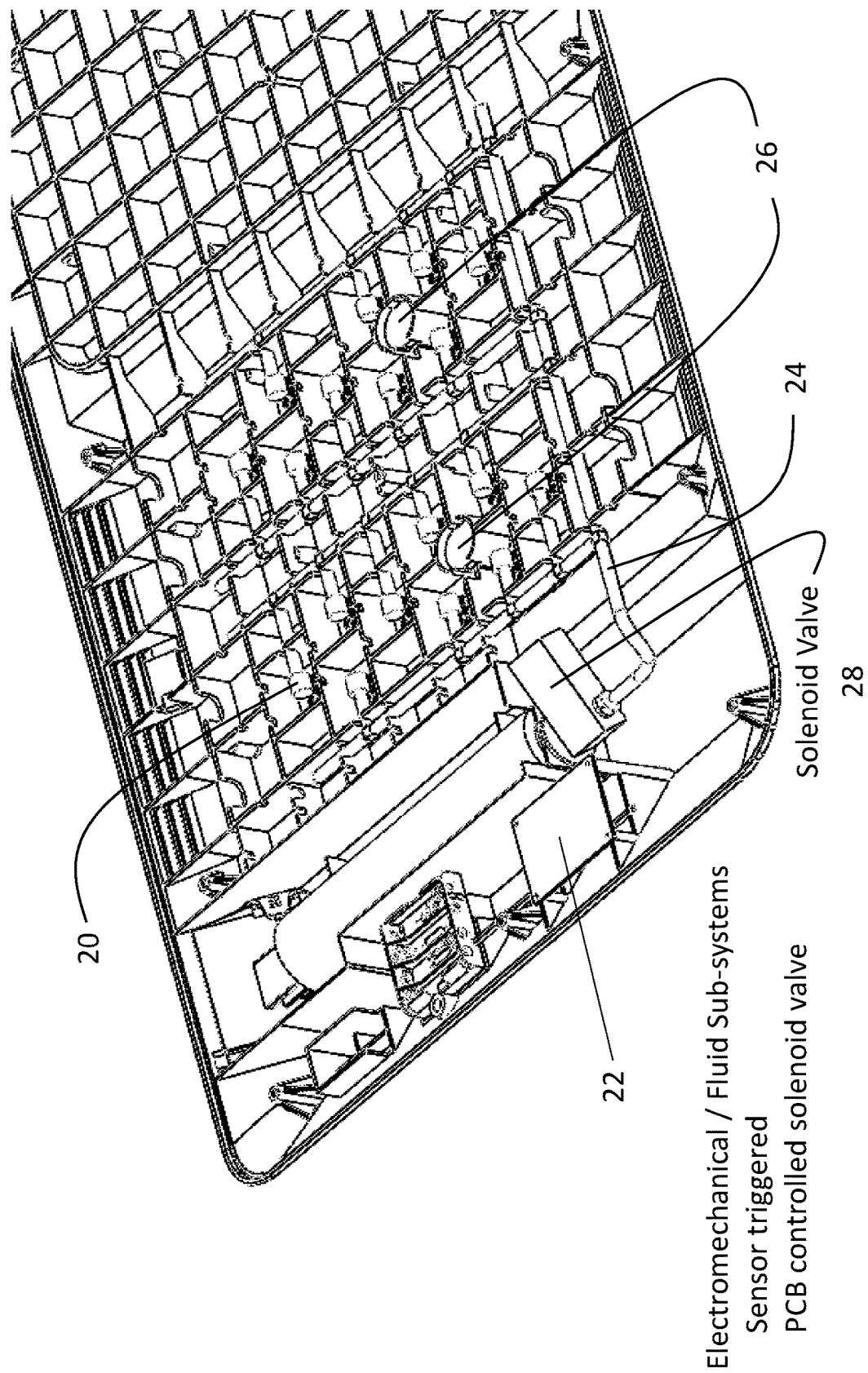
FIG. 6 is a bottom perspective view of the mat, showing the conduit 24 that carries the cleaning fluid.

Referring now to FIG. 5 and FIG. 6, FIG. 6 is a bottom perspective view of the mat, showing the conduit 24 that carries the cleaning fluid. The misting cylinder is linked, via the valve 28, to a series of conduit 24 that terminates in one or more spray nozzles 20 (see FIG. 6). Thus, when the valve 28 is opened (in response to the sensor 26 sensing that a user has stepped onto the misting area, and the microcontroller sending a signal that opens the valve), cleaning solution under pressure exits the misting cylinder, passes through the conduit 24 and exits the spray nozzles 20 in the form of a fine mist. The mist then passes through the perforations 18 and makes contact with the soles of the user's shoes. The conduit and nozzles can be made of any suitable material, such as the plastics mentioned above or metal (such as the conduit conventionally used in automobile brake lines).

Figure 7:
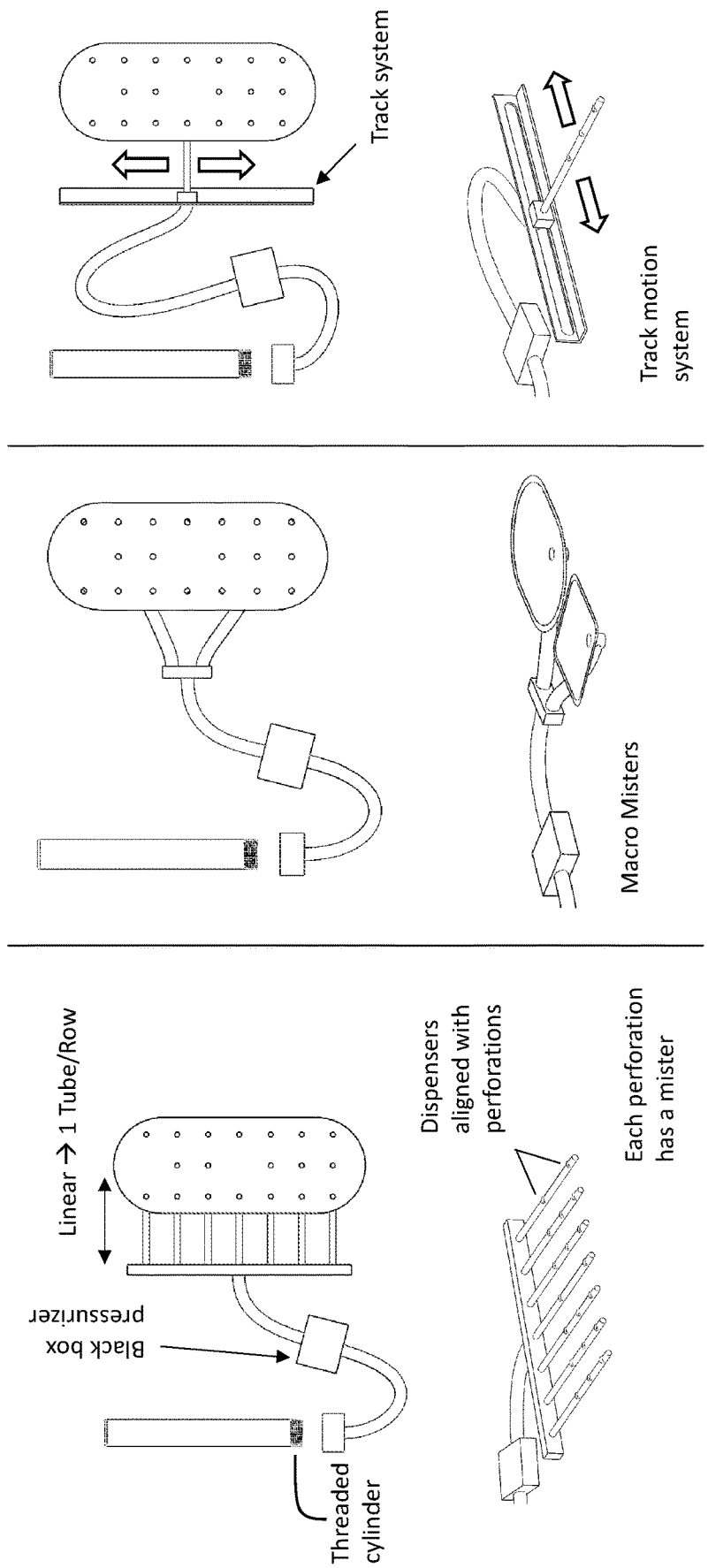
FIG. 7 depicts an alternative arrangement for the misting sub-assembly.
Figures 8A, 8B:
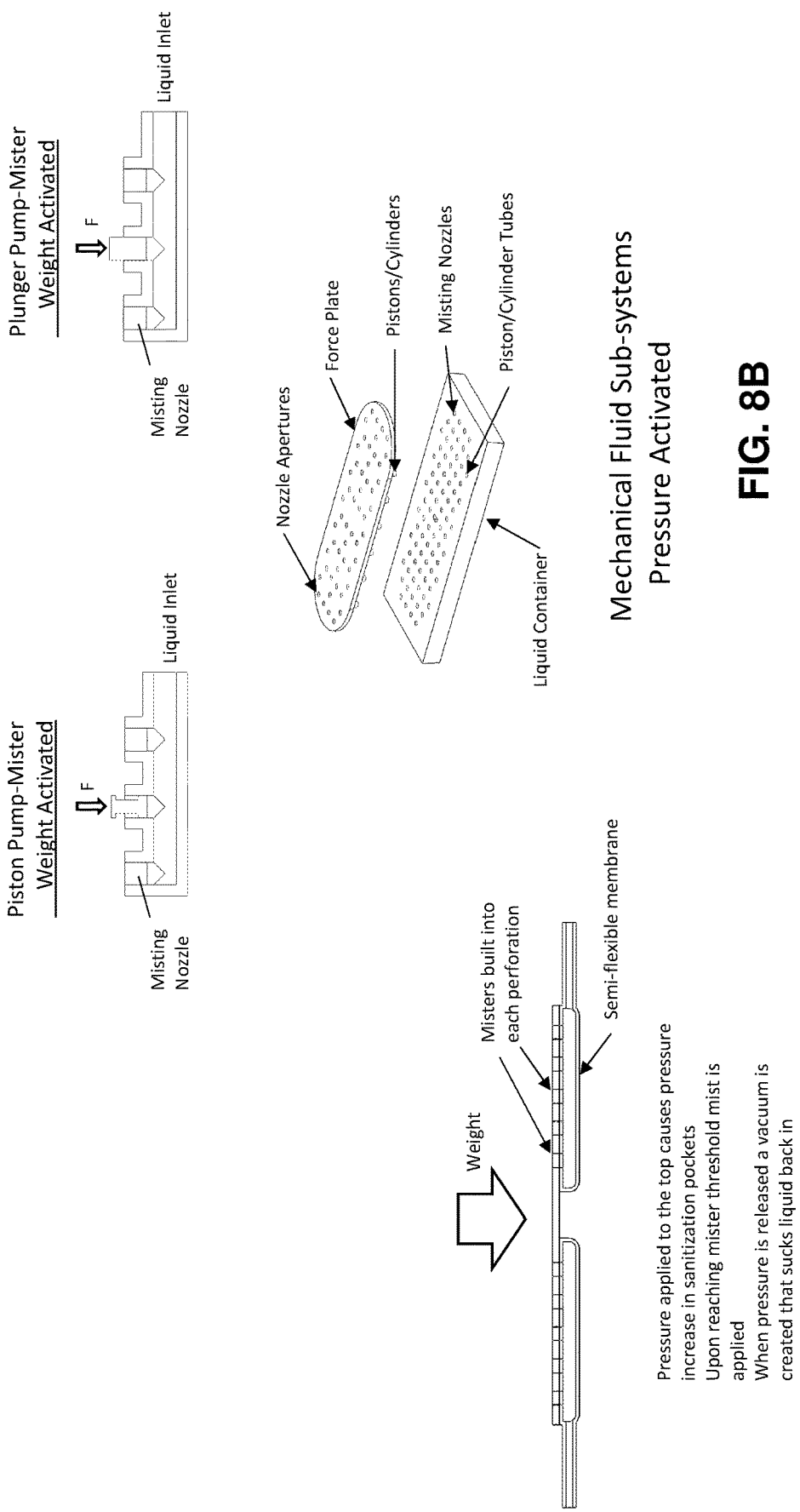
FIGS. 8A and 8B depict a pressure-actuated and a piston-actuated misting sub-assembly, respectively.

FIG. 7 depicts an alternative arrangement for the misting sub-assembly. Here, the cleaning solution is dispensed into a plenum chamber (left-hand and right-hand sides of FIG. 7) or into a series of inverted funnels or cones (center of FIG. 7). In both versions, the plenum or funnel/cone provides a volume of space for the pressurized cleaning solution to expand (and for the propellant to evaporate). These versions may ensure a more uniform application of the cleaning solution to the user's shoes. In addition, the misting sub-assembly could be dynamic and cover the surface area of the user's shoes by spraying while moving along it's width or length (right-hand side of FIG. 7).

FIGS. 8A, 8B, 9A, and 9B depict another version of the entryway mat that utilizes a piston-actuated misting sub-assembly. FIG. 9A is a top plan view of the piston-actuated misting sub-assembly. FIG. 9B is a front elevation cross-section view of the top plan view shown in FIG. 9A. As shown in these figures, the misting area comprises an upper plate 30 that is operationally connected to the main housing of the mat via a series of pistons 32 that are operably connected to the misting cylinder 13. The pistons 32 are dimensioned and configured to pressurize the misting cylinder 13 and conduit 24 when a user's weight actuates the pistons. At rest, the misting cylinder and conduit contain the cleaning solution at atmospheric pressure. When a user steps on the misting area 14, the upper plate 30 and pistons 32 place pressure on a bladder 13' that is in fluid communication with the misting cylinder 13, conduit 24, and spray nozzles 20. In this fashion, pressure placed on the upper plate 30 (by virtue of the user stepping onto the misting area 14) forces cleaning solution from the misting cylinder 13, through the conduit 24, out of the nozzles 20, where it then passes through the perforations 18 to make contact with the soles of the user's shoes.

Figure 10:
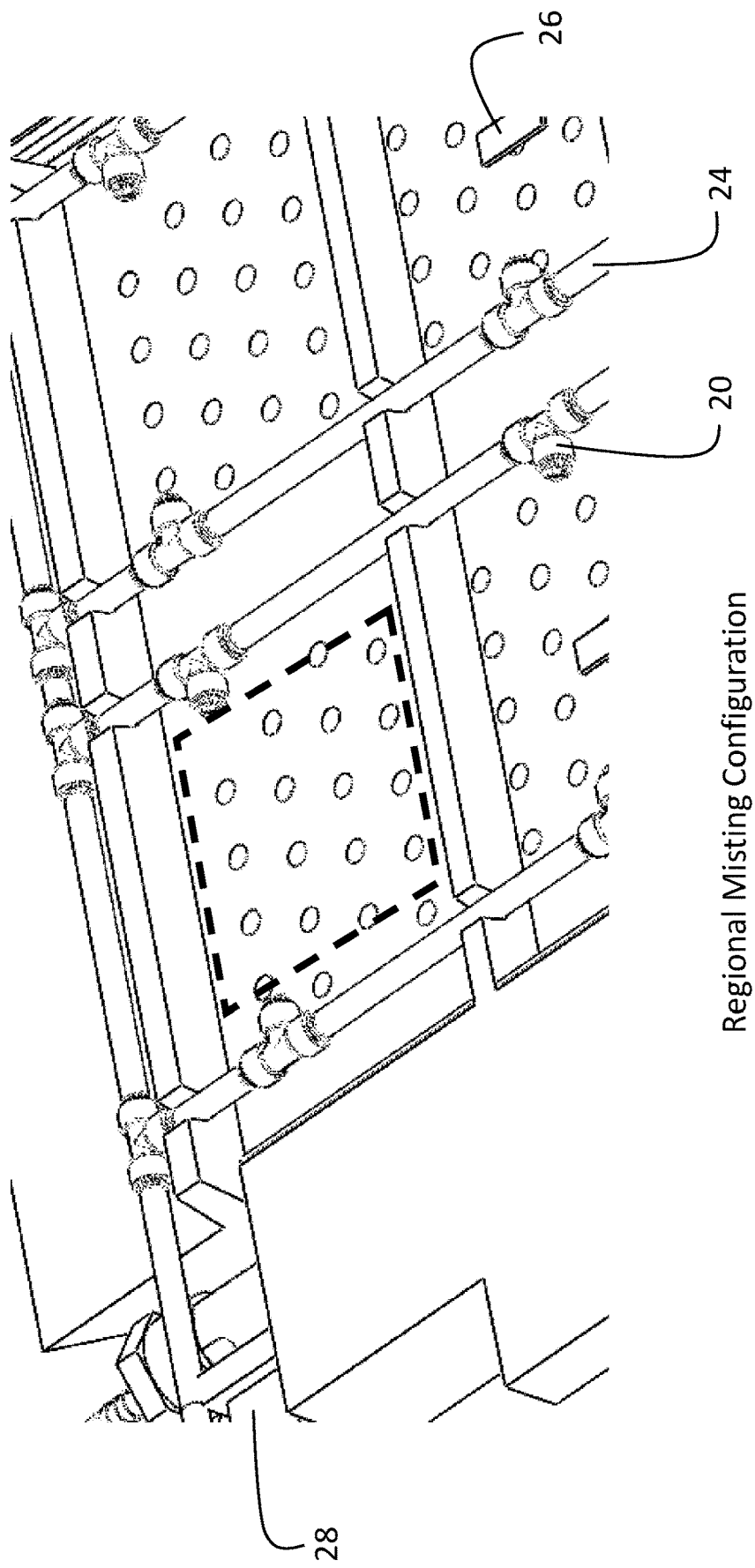
FIG. 10 is a magnified, bottom perspective view of the misting sub-assembly.

FIG. 10 is a magnified, bottom perspective view of the misting sub-assembly. FIG. 10 shows one possible arrangement of the spray nozzles 20 with respect to the perforations 18. Not every perforation 18 gets its own dedicated spray nozzle 20. Instead, the nozzles are distributed "regionally," so that the cleaning solution passes more or less in a uniform amount through the perforations.

Figure 11A:
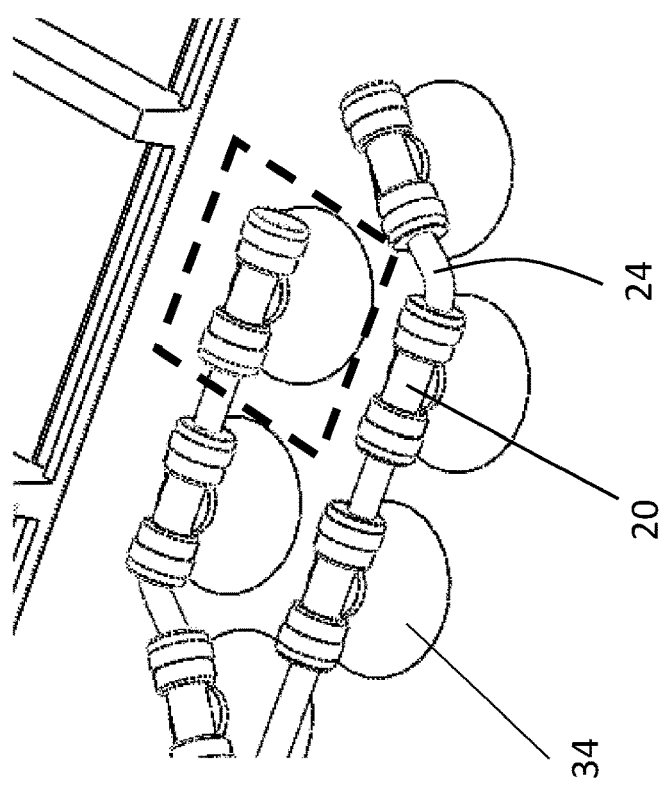
FIG. 11A is a bottom perspective view of another version of the misting sub-assembly.
Figure 11B:
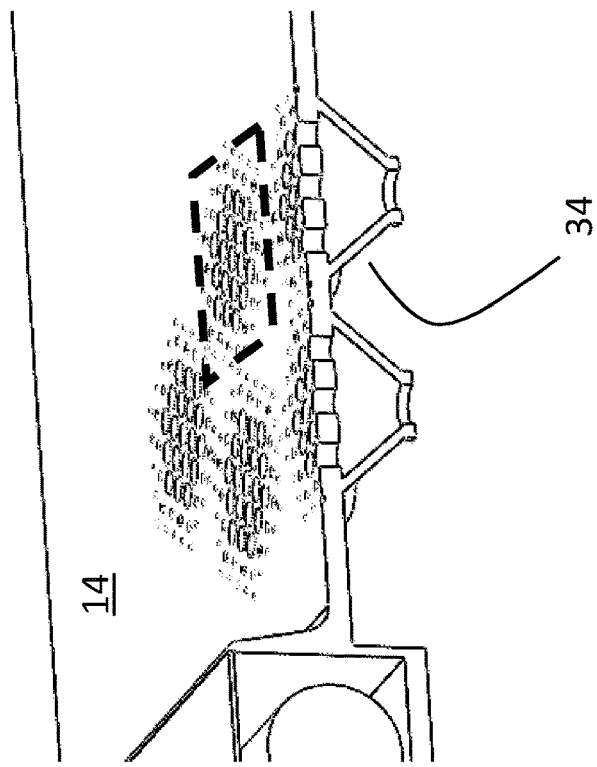
FIG. 11B is a front elevation perspective view of FIG. 11A.

FIG. 11A is a bottom perspective view of another version of the misting sub-assembly that is shown in the center panel of FIG. 7. FIG. 11B is a front elevation perspective view of FIG. 11A. Here, each nozzle 20 is operationally connected to the narrow end of a funnel or cone 34. The wide end of each funnel 34 is then in fluid connection with one or more of perforations 18. See FIG. 11B. In this fashion, the output of each nozzle 20, rather than being distributed "regionally," is dispense only through those perforations 18 encompassed by the wide end of each funnel. This version of the device provides for more accurate metering of the cleaning solution because the funnels 34 function to direct the cleaning solution through only a pre-determined number of perforations 18. (As contrasted to the cleaning solution diffusing through the nearest perforations, as is the case in the "regional" configuration of nozzles.)

Figure 12:
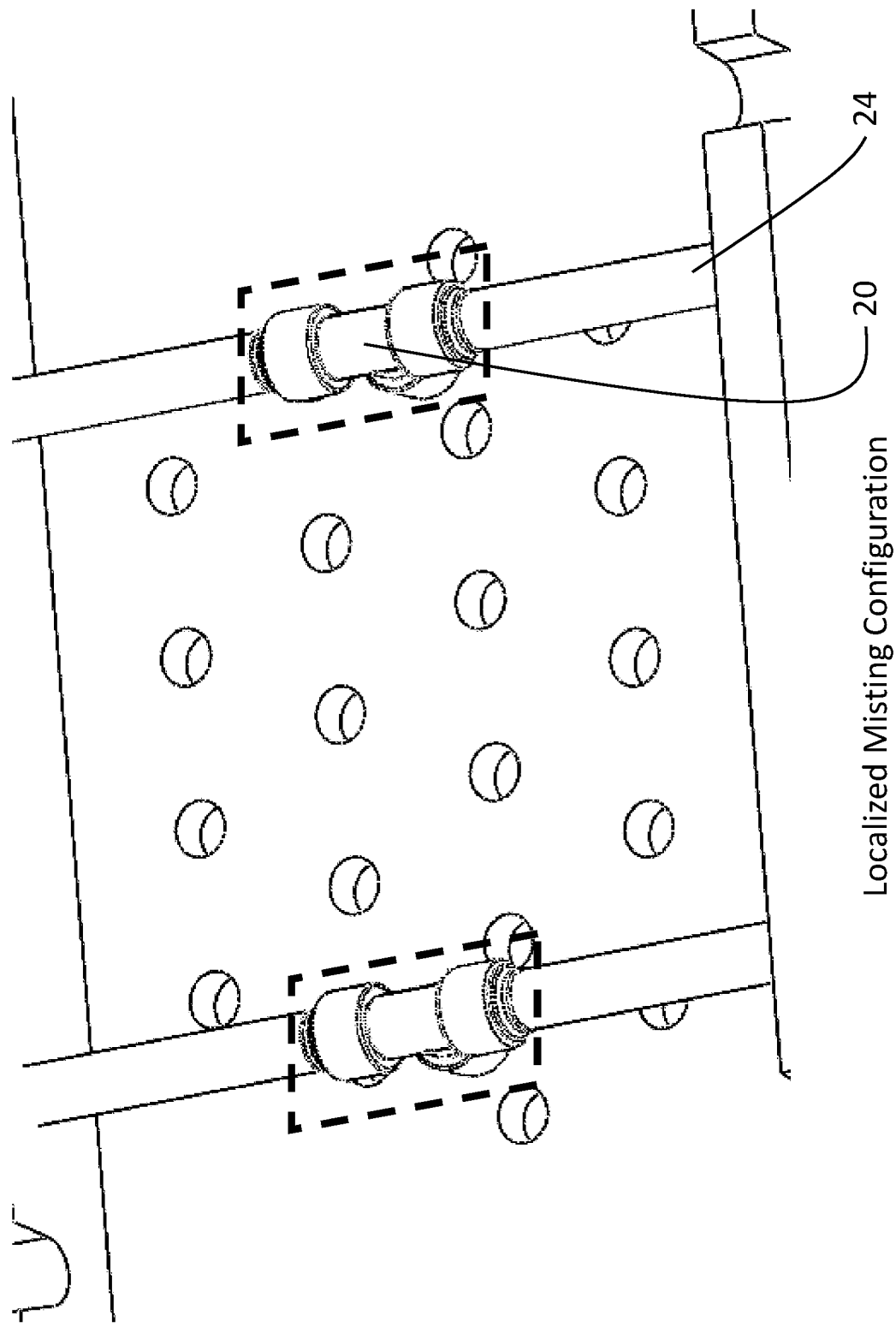
FIG. 12 is magnified, bottom perspective view of a localized misting sub-assembly.

FIG. 12 is magnified, bottom perspective view of a localized misting sub-assembly. The spray nozzle 20 is positioned in close proximity to the perforations 18. In this fashion, cleaning solution exiting the nozzles under pressure is forced upward, through the perforations. Here, the funnels 34 are eliminated and each nozzle 20 is operationally linked with just one, dedicated perforation.

Figure 13:
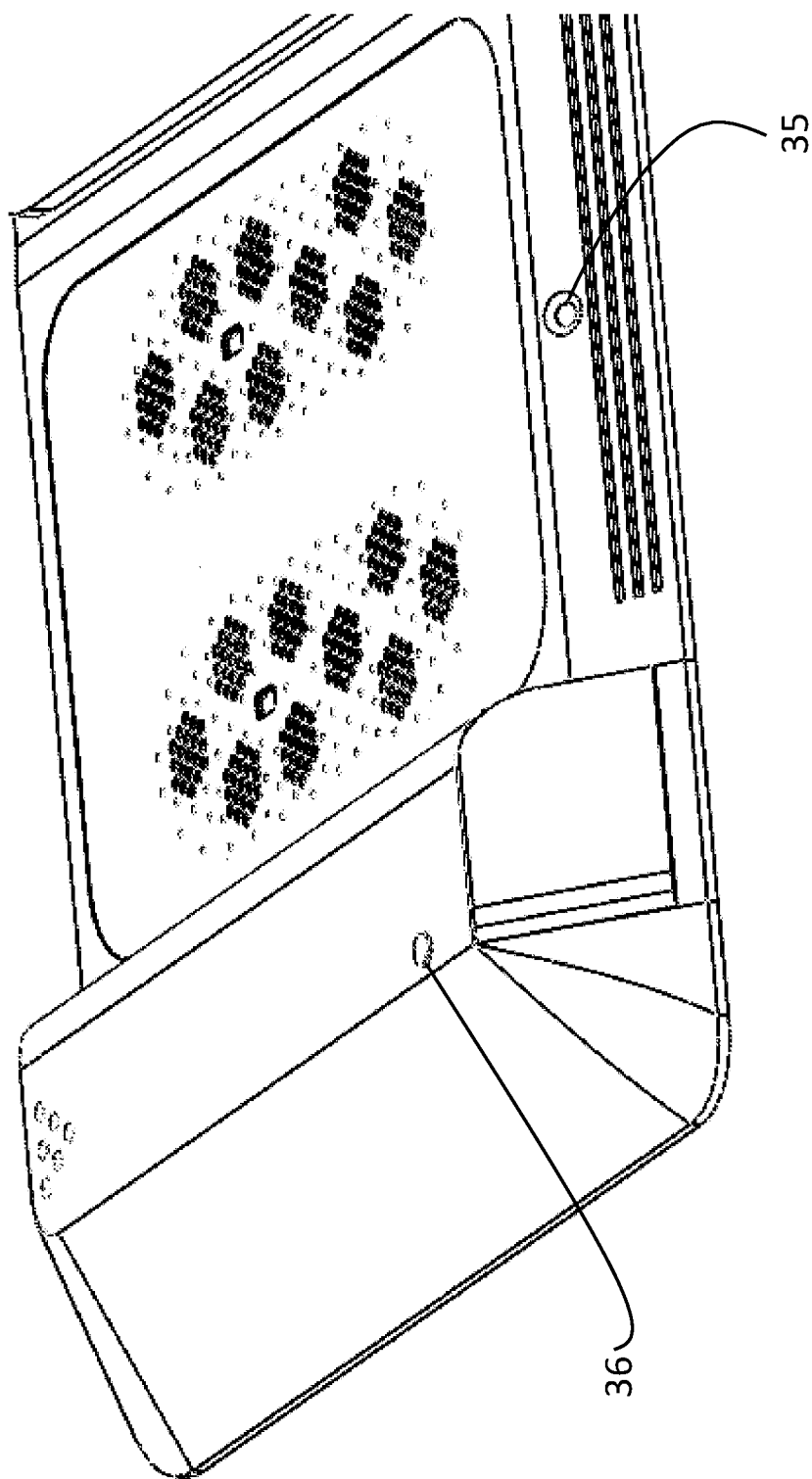
FIG. 13 is a top perspective view of the mat, showing the switch and motion sensor.

FIG. 13 is a top perspective view of one version of the mat. On the left side of the figure can be seen a switch 36, that is operationally linked to the microcontroller 22 (not shown in figure). The switch 36 is of conventional design. The switch 36 may be a toggle, push-button, momentary, latching or other type and may also have an integrated LED. The switch 36 is operationally linked to the microcontroller 22 programmed such that the switch 36 will turn the system on or off when pressed, opposite the current state. In addition, the switch 36 may be pressed for a predefined period of time which will open the valve 28 for as long as the switch 36 continues to remain pressed. In the middle of the figure can be seen a motion sensor 35, that is operationally linked to the microcontroller 22. The motion sensor 35 is of conventional design and may be of the same type as the sensor 26 or different as in the case of a PIR or other detector. The microcontroller 22 is operationally linked to the motion sensor 35 and is pre-programmed to provide power to the sensor 26 and the sensor-controlled valve 28 for a predefined period of time when the motion sensor 35 detects motion and to not provide power to the sensor 26 and the sensor-controlled valve 28 when the motion sensor 35 does not detect motion after that predefined period of time has elapsed. The microcontroller 22 will also enter into a power-saving "sleep" mode after that predefined period of time has elapsed.

What is claimed is:

1. An entryway mat comprising:
a housing defining a misting area (14) and a drying area (16), wherein the misting and drying areas are dimensioned and configured to support a human user standing on either area;
the misting area (14) defining a plurality of perforations (18) passing through it;
a misting cylinder (13) or misting bladder (13') containing a disinfecting solution at a pressure higher than atmospheric pressure and in fluid connection to one or more spray nozzles (20), wherein the one or more spray nozzles (20) are dimensioned and configured to dispense the disinfecting solution through the perforations (18) in the misting area (14) and to contact the feet or the soles of the shoes of users standing on the misting area (14);
at least one sensor (26) operationally connected to at least one sensor-controlled valve (28), wherein the at least one sensor-controlled valve (28) is operationally positioned between the misting cylinder (13) or misting bladder (13') and the one or more spray nozzles (20), wherein the at least one sensor is configured to open the at least one sensor-controlled valve (28) when a user steps onto the misting area (14) and to close the at least one sensor-controlled valve when the user steps off the misting area (14);
a microcontroller (22) operationally connected to the at least one sensor (26) and the at least one sensor-controlled valve (28), wherein the microcontroller (22) is pre-programmed to open the at least one sensor-controlled valve (28) for a pre-determined amount of time in response to a user stepping onto the misting area (14); and
a switch (36) operationally connected to the microcontroller (22), wherein the microcontroller is pre-programmed to open the at least one sensor-controlled valve (28) after the switch (36) is pressed for a predefined period of time after which the at least one sensor-controlled valve (28) will remain open as long as the switch (36) continues to remain pressed.

2. The entryway mat of claim 1, further comprising a motion sensor (35) operationally connected to the microcontroller (22), wherein the microcontroller is pre-programmed to turn on the at least one sensor (26) and the at least one sensor-controlled valve (28) when motion is detected by the motion sensor (35) and to turn off the at least one sensor (26) and the at least one sensor-controlled valve (28) and enter power-saving mode when motion is not detected by the motion sensor (35) after a predefined period of time.

3. The entryway mat of claim 1, wherein the misting area (14) comprises a movable upper plate (30) and at least one piston (32) operationally connected to the movable upper plate (30) and the misting cylinder (13) or the misting bladder (13') such that a user stepping onto the movable upper plate (30) applies pressure to the misting cylinder (13) or the misting bladder (13') via action of the at least one piston (32).

4. The entryway mat of claim 1, further comprising a number of cones (34) corresponding to the number of spray nozzles (20), each cone having a narrow end attached to its corresponding nozzle and a wide end positioned in proximity to the perforations in the misting area.

5. The entryway mat of claim 1, wherein the misting cylinder (13) or misting bladder (13') are refillable or replaceable.

6. The entryway mat of claim 5, further comprising a number of cones (34) corresponding to the number of spray nozzles (20), each cone having a narrow end attached to its corresponding nozzle and a wide end positioned in proximity to the perforations in the misting area.

7. The entryway mat of claim 5, further comprising a motion sensor (35) operationally connected to the microcontroller (22), wherein the microcontroller is pre-programmed to turn on the at least one sensor (26) and the at least one sensor-controlled valve (28) when motion is detected by the motion sensor (35) and to turn off the at least one sensor (26) and the at least one sensor-controlled valve (28) and enter power-saving mode when motion is not detected by the motion sensor (35) after a predefined period of time.

8. An entryway mat comprising:
a housing defining a misting area (14) and a drying area (16), wherein the misting and drying areas are dimensioned and configured to support a human user standing on either area;
the misting area (14) defining a plurality of perforations (18) passing through it;
a misting cylinder (13) or misting bladder (13') containing a disinfecting solution at a pressure higher than atmospheric pressure and in fluid connection to one or more spray nozzles (20), wherein the one or more spray nozzles (20) are dimensioned and configured to dispense the disinfecting solution through the perforations (18) in the misting area (14) and to contact the feet or the soles of the shoes of users standing on the misting area (14)
at least one sensor (26) operationally connected to at least one sensor-controlled valve (28), wherein the at least one sensor-controlled valve (28) is operationally positioned between the misting cylinder (13) or misting bladder (13') and the one or more spray nozzles (20), wherein the at least one sensor (26) is configured to open the at least one sensor-controlled valve (28) when a user steps onto the misting area (14) and to close the at least one sensor-controlled valve (28) when the user steps off the misting area (14);
wherein the misting area (14) comprises a movable upper plate (30) and at least one piston (32) operationally connected to the movable upper plate (30) and the misting cylinder (13) or the misting bladder (13') such that a user stepping onto the movable upper plate (30) applies pressure to the misting bladder (13') via action of the at least one piston (32); and
further comprising a number of cones (34) corresponding to the number of spray nozzles (20), each cone having a narrow end attached to its corresponding nozzle and a wide end positioned in proximity to the perforations in the misting area.

9. The entryway mat of claim 8, wherein the misting cylinder (13) or misting bladder (13') are refillable or replaceable.

10. The entryway mat of claim 8, further comprising a microcontroller (22) operationally connected to the at least one sensor (26) and the at least one sensor-controlled valve (28), wherein the microcontroller (22) is pre-programmed to open the at least one one sensor-controlled valve (28) for a pre-determined amount of time in response to a user stepping onto the misting area (14).

11. The entryway mat of claim 10, further comprising a motion sensor (35) operationally connected to the microcontroller (22), wherein the microcontroller is pre-programmed to turn on the at least one sensor (26) and the at least one sensor-controlled valve (28) when motion is by the motion sensor (35) detected and to turn off the at least one sensor (26) and the at least one sensor-controlled valve (28) and enter power-saving mode when motion is not detected by the motion sensor (35) after a predefined period of time.

12. The entryway mat of claim 10, further comprising a switch (36) operationally connected to the microcontroller (22), wherein the microcontroller is pre-programmed to open the at least one sensor-controlled valve (28) after the switch (36) is pressed for a predefined period of time after which the at least one sensor-controlled valve (28) will remain open as long as the switch (36) continues to remain pressed.

13. An entryway mat comprising:
- a housing defining a misting area (14) and a drying area (16), wherein the misting and drying areas are dimensioned and configured to support a human user standing on either area;
- the misting area (14) defining a plurality of perforations (18) passing through it;
- a misting cylinder (13) or misting bladder (13') containing a disinfecting solution at a pressure higher than atmospheric pressure and in fluid connection to one or more spray nozzles (20), wherein the one or more spray nozzles (20) are dimensioned and configured to dispense the disinfecting solution through the perforations (18) in the misting area (14) and to contact the feet or the soles of the shoes of users standing on the misting area (14);
- at least one sensor (26) operationally connected to at least one sensor-controlled valve (28), wherein the at least one sensor-controlled valve (28) is operationally positioned between the misting cylinder (13) or misting bladder (13') and the one or more spray nozzles (20), wherein the at least one sensor is configured to open the at least one sensor-controlled valve (28) when a user steps onto the misting area (14) and to close the at least one sensor-controlled valve when the user steps off the misting area (14);
- a microcontroller (22) operationally connected to the at least one sensor (26) and the at least one sensor-controlled valve (28), wherein the microcontroller (22) is pre-programmed to open the at least one sensor-controlled valve (28) for a pre-determined amount of time in response to a user stepping onto the misting area (14);
- wherein the misting area (14) comprises a movable upper plate (30) and at least one piston (32) operationally connected to the movable upper plate (30) and the misting cylinder (13) or the misting bladder (13') such that a user stepping onto the movable upper plate (30) applies pressure to the misting cylinder (13) or the misting bladder (13') via action of the at least one piston (32); and
- further comprising a number of cones (34) corresponding to the number of spray nozzles (20), each cone having a narrow end attached to its corresponding nozzle and a wide end positioned in proximity to the perforations in the misting area.

* * * * *